(12) United States Patent
Liu

(10) Patent No.: US 6,486,169 B1
(45) Date of Patent: Nov. 26, 2002

(54) BOTANICAL DRUG FOR TREATMENT AND PREVENTION OF ALZHIMER'S DISEASE

(76) Inventor: Yaguang Liu, 67-08 168th St., Flushing, NY (US) 11365

( * ) Notice: Subject to any disclaimer, the term of this patent is extended or adjusted under 35 U.S.C. 154(b) by 0 days.

(21) Appl. No.: 10/078,335

(22) Filed: Feb. 19, 2002

(51) Int. Cl.$^7$ ................. A61K 35/78; A61K 31/44; A01N 43/42

(52) U.S. Cl. ............... 514/295; 424/725; 514/290; 514/423; 514/425; 546/98; 548/530; 548/539; 548/543; 548/544; 548/555

(58) Field of Search ............... 546/93; 548/530, 548/539, 544, 543, 551, 555; 424/725; 514/290, 425, 295, 423

(56) References Cited

U.S. PATENT DOCUMENTS 4,731,456 A  * 3/1988 Hartwig ............... 548/544

* cited by examiner

*Primary Examiner*—Herbert J. Lilling

(57) ABSTRACT

The present invention related to safe botanical drug for treatment and prevention of Alzheimer's disease. Specifically, this invention proves a safe botanical drug, Huperzine (HUE) and Clausenamide (CLE) and their preparation.

HUE has the following pharmaceutical functions: inhibiting acetylcholinesterase (CAT), increasing memory, decreasing Alzheimer amyloid protein, increasing RNA and protein synthesis of brain, increasing calcium in brain, decreasing superoxide anion.

CLE has the following pharmaceutical functions: increasing memory, decreasing Alzheimer amyloid protein, increasing RNA and protein synthesis of brain, increasing calcium in brain, decreasing superoxide anion, increasing long-term potentiation and increasing dopanmine (DA). It is important that HUE combined with CLE have stronger function as mentioned above.

11 Claims, No Drawings

BOTANICAL DRUG FOR TREATMENT AND PREVENTION OF ALZHIMER'S DISEASE

BACKGROUND OF THE INVENTION

This invention relates to safe botanical drug of treatment and prevention of Alzhimer's disease. Specifically, this invention provides a safe botanical drug, including Huperzine (HUE) and Clausenamide (CLE).

DESCRIPTION OF PRIOR ART

Alzhimer's disease (AD) is the commonest form of dementia in the elderly. It manifests as a progressive loss of memory, particularly recent memories, and other cognitive functions, until patients eventually become completely dependent on cares.

It is estimated that AD affects about 4–5 million Americans. The incidence of AD and other dementia doubles every 5 years beyond the age of 65, and about 50% of the United States population over the age of 85 have symptoms of AD. Death occurs inevitably after 3–15 years. AD is predominantly a disease of the elderly and it is a major medical concern in view of the fact that about 33 million Americans are 65 and older, and this number is predicted to increase to 51 million by the year 2025. The annual economic cost of AD health care expenses and lost wages (for AD patients and their caregivers) is estimated at $80–100 billion.

Patients with AD have a large loss of neurons, in both cortical and subcortical regions. Brain weight is reduced by 30–40%. Many patients with AD have a large reduction of cholinergic neurons. It is known that choline acetyltransferase (CAT), which is caused by the loss of cholinergic nuclei and function. AD is characterized by progressive impairment of memory and cognitive functions and may lead to a completely vegetative state. There is much evidence for a marked decrease in choline acetyltransferase and other markers of cholinergic neuron activity and for changes in brain of AD. Eventually, cholinergic and perhaps other neurons die or are destroyed. Many methods of treatment of AD have been explored. Most attention has been focused on the cholinergic drugs because of the evidence for loss of cholinergic neurons noted above. Some drugs, for example, Tacrine and Donepezil used for treatment of AD. These two drugs are cholinesterase inhibitor. The drug apparently increases the release of acetylcholine. However, Tacrine has a significant hepatic toxicity. Also, Tacrine causes nausea and vomiting and Donepezil has shortest half-life. Also, Donepezil has some side effects of peripheroneural systems.

Other important factor of AD is the βA peptide that is found in the senile plaques and cerebrovascular deposits exist as aggregate with a fibrillar appearance. So far, the result of all drug for AD are very disappointed. There still is lacking an effective and safety drug, which will treat and prevent AD and without any side effect at same time.

DETAILED DESCRIPTION OF THE INVENTION

Recent development in molecular neuroscience aspects indicated that cholinergic neurons, CAT and the β-amyloid peptide (βA) have an important act in AD. Botanical drug for treatment and prevention of Alzhimer's disease (BTA) is a new safe botanical drug. BTA contains HUE or CLE or HUE combined with CLE. HUE is an acetylcholinesterase inhibitor and the intention is to increase cholinergic transmission by preventing the breakdown of Ach liberated from the remaining cholinergic neurons. Also, HUE decreases βA.

HUE produces pharmaceutical effects by inhibiting the action of acetylcholinesterase, which hydrolyzes acetylcholine to choline and acetic acid. HUE increases the concentration of endogenous acetylcholine in brain. Therefore, patients with AD treated by HUE showed some symptomatic improvements of AD.

CLE increases long-term potentiation and improves memory and biochemistry reactivity in neuron.

Chemical structure of HUE and CLE are shown as below:

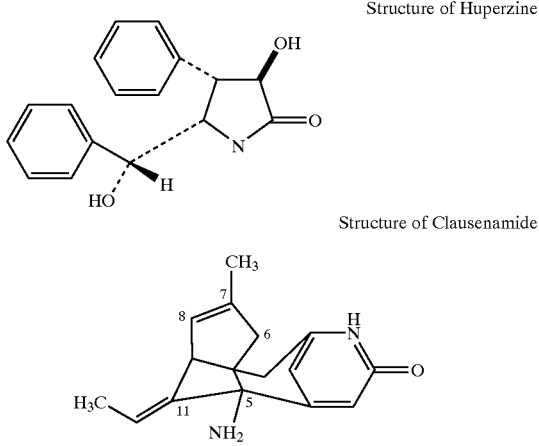

Structure of Huperzine

Structure of Clausenamide

The following specific examples will provide detailed illustrations of methods of producing relative drugs, according to the present invention and pharmaceutical dosage containing demonstrates its effectiveness in control of cancer cells. These examples are not intended, however, to limit or restrict the scope of the invention in any way, and should not be construed as providing conditions, parameters, reagents or starting materials which must be utilized exclusively in order to practice the present invention.

EXAMPLE 1

Extraction of HUE

Huperzine extracted from plant named Huperia serrata Thunb. The dried powder of plant was extracted by 95% of ethanol. The ethanol extraction was recovered under reduced pressure and still residue (1) obtained. The residue extracted by 2% of HCl. 10% of $Na_2CO_3$ added to 2% of HCl to neutrality (pH7). Neutral solution was extracted by $CHCl_3$. $CHCl_3$ was recovered under reduced pressure and still residue (2) obtained. The still residue (2) was passed through a column of silica gel and elute with ethanol-$CH_3COOH$ (100:7) under reduced pressure. Elute extracted by $CHCl_3$. $CHCl_3$ extraction was recovered under reduced pressure. And still residue was obtained. The residue was dried under vacuum. Final product is Huperzine.

EXAMPLE 2

HUE Injecting Preparation

HUE, according to the conventional methods, was made as ampoules or other injection preparation, then sterilized. Type XGI.S double door functional ampoule sterilizing machine is used for manufacturing of HUE injection. The function of facilities includes sterilization, leakage detection and washing. Microcomputer (PC machine) is applied in the principal controlling system. Dose is intramuscularly 5–100 mg daily.

EXAMPLE 3
HUE Oral Preparation

HUE powder granulated accorded to the conventional granulation method. The mixture content decreased from 100% to 93%. The 7% of content was different types of fillers. Disintegrants and lubricants were used: microcrystalline cellulose (Avicel PH 105, PH 101, PH 102, PH 200, all from FMC Corp., Lehmann and Voss and Co., Hamburg, Germany; and Vivacel 200, Rettenmaier and Söhne GmbH, Ellwangen-Holzmühle, Germany), microfine cellulose (Elcema P 050, P 100, G 250, all from Degussa AG, Frandfurt, Germany; and Tablettierhilfsmittel K, Merck KGaA, Darmstadt, Germany), lactose cellulose granulate (Cellactose, Meggle, Wasserburg, Germany), α-lactose monohydrate (Lactose D 80, Meggle, Wasserburg, Germany), and modified maize starch (Starch 1500, Colorcon GmbH, Königstein, Germany).

The disintegrants tested were the following: cross-linked sodium carboxymethyl cellulose (Ac-Di-Sol, FMC Corp./Lehmann and Voss and Co.; and Nymcel ZSB 10, Nymcel ZSB 16, METSÄ-SERLA, Njimegen, Netherlands), Cross-linked calcium carboxymethyl-cellulose (ECG 505, FMC Corp./Lehmann and Voss and Co.), potato starch (Caeleo, Hilden, Germany), sodium starch glycolate (Explotab, Gustav Parmentier, Frankfurt, Germany; and Primojel, AVEBE Deutschland, Düsseldorf, Germany), cross-linked polyvinylpyrrolidone (Kollidon CL, BASF AG, Ludwigsburg, Germany; and Polyplasdone XL, ISP Deutschland, Frechen, Germany), and low-substituted hydroxypropyl-cellulose (L-HPC LH 22, L-HPC LH 31, both from Shin-Etsu Chemical Co., Ltd., Tokyo, Japan).

For lubrication, the following were used: magnesium stearate (Otto Bärlocher GmbH, Munich, Germany), glyceryl tristearate (Dynasan 118, Hüls Ag, Witten, Germany), and polyethylene glycol (PEG 6000, Hoechst AG Frankfurt/Main, Germany).

Colloidal silicon dioxide (Cab-O-Sil M 5, Cabot GmbH, Hanau, Germany; Syloid 244, W. R. Grace and Co., Lexington, Ky., and Aerosil 200, Degussa AG, Frankfurt/Main, Germany) and hydrophobic colloidal silicon dioxide (Aerosil R 972, Degussa AG) were used. As a stabilizer, ascorbic acid (Merck KGaA, Darmstadt, Germany) was added.

The content of HUE was kept constant at a level of 100 mg per tablet. Tablet weight was varied between 100–105 mg. Tablet mixtures were mixed for 10 min in the Turbula mixer (type T2C, Willy Bachofen, Basel, Switzerland). The n lubricants were sieved through a 315-μm sieve into the mix. Final mixing was carried out for 5 min at 42 rpm in the Turbula mixer. The mixtures were compressed using a rotary press (Korsch PH 103, Korsch, Berlin). The lower compression roller was instrumented with four strain gauges (type 3/120 LY 11, Holtinger Baldwin, Inc., Darmstadt, Germany). A Philips carrier-frequency bridge (PR 9307 Philips, Kassel, Germany) was used for signal amplification. Each batch was compressed at different levels of compression force in the range of 1 to 25 kN. As a stabilizer, ascorbic acid (Merk KGaA, Darmstadt, Germany) was added. Sugar-coating operation was also performed conventionally.

The dosage of HUE is orally 50–200 mg daily.

EXAMPLE 4
Extraction of CLE

CLE was extracted from Clausena lansium (Lour) Skeels and other Clausena. 5 L. of water was added to 1 kg of dried powder of Clausena lansium (Lour) Skeels. The mixture was heated to boil and simmered for 1.5 hours after boiling. This water extraction was repeated once and the two extracts were combined and filtered. The filtrate was concentrated under reduced pressure to approximately 300 ml and silica gel was added to the concentrate and mixed. Silica gel was dried under reduced pressure. Silica gel extracted with $CCl_4$, then $CCl_4$ concentrated under reduced pressure. Crystal was obtained. The crystal was recrystalized from $CH_3OH$. Crystal dried under reduced pressure. The final product is CLE.

EXAMPLE 5
CLE Injecting Preparation

CLE, according to the conventional methods, was made as ampoules or other injection preparation, then sterilized. Type XGI.S double door functional ampoule sterilizing machine is used for manufacturing of CLE injection. The function of facilities includes sterilization, leakage detection and washing. Microcomputer (PC machine) is applied in the principal controlling system. Dose is intramuscularly 5–100 mg daily.

EXAMPLE 6
CLE Oral Preparation

CLE powder granulated accorded to the conventional granulation method. The mixture content decreased from 100% to 93%. The 7% of content was different types of fillers. Disintegrants and lubricants were used: microcrystalline cellulose (Avicel PH 105, PH 101, PH 102, PH 200, all from FMC Corp., Lehmann and Voss and Co., Hamburg, Germany; and Vivacel 200, Rettenmaier and Söhne GmbH, Ellwangen-Holzmühle, Germany), microfine cellulose (Elcema P 050, P 100, G 250, all from Degussa AG, Frandfurt, Germany; and Tablettierhilfsmittel K, Merck KGaA, Darmstadt, Germany), lactose cellulose granulate (Cellactose, Meggle, Wasserburg, Germany), α-lactose monohydrate (Lactose D 80, Meggle, Wasserburg, Germany), and modified maize starch (Starch 1500, Colorcon GmbH, Königstein, Germany).

The disintegrants tested were the following: cross-linked sodium carboxymethyl cellulose (Ac-Di-Sol, FMC Corp./Lehmann and Voss and Co.; and Nymcel ZSB 10, Nymcel ZSB 16, METSÄ-SERLA, Njimegen, Netherlands), Cross-linked calcium carboxymethyl-cellulose (ECG 505, FMC Corp./Lehmann and Voss and Co.), potato starch (Caeleo, Hilden, Germany), sodium starch glycolate (Explotab, Gustav Parmentier, Frankfurt, Germany; and Primojel, AVEBE Deutschland, Düsseldorf, Germany), cross-linked polyvinylpyrrolidone (Kollidon CL, BASF AG, Ludwigsburg, Germany; and Polyplasdone XL, ISP Deutschland, Frechen, Germany), and low-substituted hydroxypropyl-cellulose (L-HPC LH 22, L-HPC LH 31, both from Shin-Etsu Chemical Co., Ltd., Tokyo, Japan).

For lubrication, the following were used: magnesium stearate (Otto Bärlocher GmbH, Munich, Germany), glyceryl tristearate (Dynasan 118, Hüls Ag, Witten, Germany), and polyethylene glycol (PEG 6000, Hoechst AG Frankfurt/Main, Germany).

Colloidal silicon dioxide (Cab-O-Sil M 5, Cabot GmbH, Hanau, Germany; Syloid 244, W. R. Grace and Co., Lexington, Ky., and Aerosil 200, Degussa AG, Frankfurt/Main, Germany) and hydrophobic colloidal silicon dioxide (Aerosil R 972, Degussa AG) were used. As a stabilizer, ascorbic acid (Merck KGaA, Darmstadt, Germany) was added.

The content of CLE was kept constant at a level of 100 mg per tablet. Tablet weight was varied between 100–105 mg. Tablet mixtures were mixed for 10 min in the Turbula mixer (type T2C, Willy Bachofen, Basel, Switzerland). The n lubricants were sieved through a 315-μm sieve into the mix. Final mixing was carried out for 5 min at 42 rpm in the Turbula mixer. The mixtures were compressed using a rotary press (Korsch PH 103, Korsch, Berlin). The lower compression roller was instrumented with four strain gauges (type 3/120 LY 11, Holtinger Baldwin, Inc., Darmstadt, Germany). A Philips carrier-frequency bridge (PR 9307 Philips, Kassel, Germany) was used for signal amplification. Each batch was compressed at different levels of compression force in the range of 1 to 25 kN. As a stabilizer, ascorbic acid (Merk KGaA, Darmstadt, Germany) was added. Sugar-coating operation was also performed conventionally.

The dosage of CLE is orally 50–200 mg daily.

EXAMPLE 7
BTA Injecting Preparation

50% of HUE and 50% of CLE, according to the conventional methods, was made as ampoules or other injection preparation, then sterilized. Type XGI.S double door functional ampoule sterilizing machine is used for manufacturing of BTA injection. The function of facilities includes sterilization, leakage detection and washing. Microcomputer (PC machine) is applied in the principal controlling system. Dose is intramuscularly 5–100 mg daily.

EXAMPLE 8
BTA Oral Preparation

50% of HUE and 50% of CLE powder granulated accorded to the conventional granulation method. The mixture content decreased from 100% to 93%. The 7% of content was different types of fillers. Disintegrants and lubricants were used: microcrystalline cellulose (Avicel PH 105, PH 101, PH 102, PH 200, all from FMC Corp., Lehmann and Voss and Co., Hamburg, Germany; and Vivacel 200, Rettenmaier and Sohne GmbH, Ellwangen-Holzmühle, Germany), microfine cellulose (Elcema P 050, P 100, G 250, all from Degussa AG, Frandfurt, Germany; and Tablettierhilfsmittel K, Merck KGaA, Darmstadt, Germany), lactose cellulose granulate (Cellactose, Meggle, Wasserburg, Germany), α-lactose monohydrate (Lactose D 80, Meggle, Wasserburg, Germany), and modified maize starch (Starch 1500, Colorcon GmbH, Königstein, Germany).

The disintegrants tested were the following: cross-linked sodium carboxymethyl cellulose (Ac-Di-Sol, FMC Corp./Lehmann and Voss and Co.; and Nymcel ZSB 10, Nymcel ZSB 16, METSÄ-SERLA, Njimegen, Netherlands), Cross-linked calcium carboxymethyl-cellulose (ECG 505, FMC Corp./Lehmann and Voss and Co.), potato starch (Caeleo, Hilden, Germany), sodium starch glycolate (Explotab, Gustav Parmentier, Frankfurt, Germany; and Primojel, AVEBE Deutschland, Düsseldorf, Germany), cross-linked polyvinylpyrrolidone (Kollidon CL, BASF AG, Ludwigsburg, Germany; and Polyplasdone XL, ISP Deutschland, Frechen, Germany), and low-substituted hydroxypropyl-cellulose (L-HPC LH 22, L-HPC LH 31, both from Shin-Etsu Chemical Co., Ltd., Tokyo, Japan).

For lubrication, the following were used: magnesium stearate (Otto Barlocher GmbH, Munich, Germany), glyceryl tristearate (Dynasan 118, Hüls Ag, Witten, Germany), and polyethylene glycol (PEG 6000, Hoechst AG Frankfurt/Main, Germany).

Colloidal silicon dioxide (Cab-O-Sil M 5, Cabot GmbH, Hanau, Germany; Syloid 244, W. R. Grace and Co., Lexington, Ky., and Aerosil 200, Degussa AG, Frankfurt/Main, Germany) and hydrophobic colloidal silicon dioxide (Aerosil R 972, Degussa AG) were used. As a stabilizer, ascorbic acid (Merck KGaA, Darmstadt, Germany) was added.

The content of BTA was kept constant at a level of 100 mg per tablet. Tablet weight was varied between 100–105 mg. Tablet mixtures were mixed for 10 min in the Turbula mixer (type T2C, Willy Bachofen, Basel, Switzerland). The n lubricants were sieved through a 315-μm sieve into the mix. Final mixing was carried out for 5 min at 42 rpm in the Turbula mixer. The mixtures were compressed using a rotary press (Korsch PH 103, Korsch, Berlin). The lower compression roller was instrumented with four strain gauges (type 3/120 LY 11, Holtinger Baldwin, Inc., Darmstadt, Germany). A Philips carrier-frequency bridge (PR 9307 Philips, Kassel, Germany) was used for signal amplification. Each batch was compressed at different levels of compression force in the range of 1 to 25 kN. As a stabilizer, ascorbic acid (Merk KGaA, Darmstadt, Germany) was added. Sugar-coating operation was also performed conventionally. The dosage of BTA is orally 50–200 mg daily.

EXAMPLE 9
Effect of HUE on CAT

Male Sprague-Dawley rats, 180–220 g used in experiments. Twenty rats of HUE group were injected HUE at 0.1, 0.5 and 1.0 mg/kg and 20 rats of control group were injected at same value of saline. Rats were decapitated and the brains rapidly removed and placed on a glass plate set in ice at $-25°$ C. Dissected material was stored at $-25°$ C. until use.

All chemicals were analytical grade where obtainable. n-Butanol was acidified by adding 0.85 ml concentrated HCl to 1 liter of n-butanol. Solid OPT and L-cysteine were stored at $-25°$ C. until use. 0.004% m/v OPT in 10 N HCL, 0.1% w/v cysteine in 0.1% N HCl, 0.1% w/v cysteine in deionized water, and 0.1% w/v OPT in methanol were all prepared immediately before use. Thus whole brain, cortex, hippocampus, striatum or other part of brain were separated, then homogenized in cold acidified n-butanol.

To remove endogenous acetyl acceptors, homogenates were dialysed, in pre-washed tubing, against two changes of 200 volumes of 50 mM Tris-HCl buffer pH 7.4 containing 0.5 mM dithiothreitol and 0.1 mM EDTA for a total of 18 at 4° C. the incubation tubes contained, in addition to enzyme, 0.24 mM radioactive acetyl-CoA, 10 mM choline, 0.18 M NaCl, 0.9 mM EDTA, 0.05 mM dithiothreitol, depending on the brain region 0.1 mM or 0.2 mM neostigmine methyl sulphate, 0.05 per cent (w/v) bovine serum albumin, 0.5 per cent (v/v) Triton X-100, 1.67 mM Tris, 45 mM sodium phosphate buffer, final pH 7.0. After incubation the samples wee processed, the volume of the column and total elution volume being increased to 0.6×4.5 cm and 3 ml, respectively. CAT was determined.

TABLE 1

Effect of HUE on CAT

| Group | mg/kg | CAT inhibition (%) | | |
|---|---|---|---|---|
| | | Cortex | Hippocampus | Striatum |
| Control | 0 | 0 | 0 | 0 |
| HUE (1) | 0.10 | 18 ± 2 | 15 ± 2 | 20 ± 3 |
| HUE (2) | 0.20 | 28 ± 3 | 26 ± 3 | 29 ± 4 |
| HUE (3) | 0.40 | 41 ± 5 | 36 ± 4 | 38 ± 4 |

The data of Table 1 indicated that HUE has significantly inhibited CAT. Therefore, HUE could increase acetylcholine in brains.

EXAMPLE 10
Effect of HUE on Alzheimer Amyloid Protein

In AD, the protein forms aggregates of insoluble β-pleated sheets of fibrillar βA protein(amyloid). The conformational change from soluble to fibrillar forms seems to be a spontaneous event. The fibrillization is increased with higher concentrations of βA and with the longer forms of βA, so any production of larger amounts of βA than normal or production of the larger, less soluble forms of βA will tend to increase plaque formation. Once the βA plaque has started to form, other molecules can interact with the nascent plaque to produce eventually the mature plaque with its associated areas of cell death. In present study, effect of HUE on neuroblastoma cells exposed to the Alzheimer amyloid β protein and Aβ was examined.

N2a neuroblastoma cells were cultured and then exposed to 50 μm Aβ for 24 hours.

Concentration of HUE was 50 μg/ml. Cells viability determined by fluorescent staining, iodide and the trypan blue exclusion methods were used in experiments.

The data are shown as the following table.

TABLE 2

Effect of HUE and CLE on Alzheimer amyloid protein.

| Group | Cells viability (%) |
|---|---|
| Normal | 97.5 |
| Amyloid β protein (βA) | 35.4 |
| HUE + βA | 80.2* |
| CLE + βA | 70.5* |
| HUE + CLE + βA | 8.97* |

*P < 0.01 as compared with amyloid βA group

The data of Table 2 indicated that addition of HUE to neuroblastoma cells exposed to βA showed a markedly increase in cells survival. Also, CLE strengthens the action of HUE.

EXAMPLE 11
Effect of HUE and CLE on Memory

Alzheimer's disease (AD) is the commonest form of dementia in the elderly. It manifests as a progressive loss of memory, particular recent memories. Therefore, return of memory is a key index of treating AD.

Four months of male mice of PBA/2 strains used in experiments. Most behaviors measures had a large activity decline with advancing age. Mice of HUE group were injected 0.1, 0.5 and 1.0 mg/kg of HUE. The control group was injected saline. Complex learning measures and memory were determined in experiments. (Reference see "Mammalian Models for Research on Aging", pp 23–180, edited by Committee on Animal Models for Research on Aging, Institute of Laboratory Animal resources, division of Biological Sciences and Assembly of Life Science, published by National Academy Press, Washington, D.C., 1981). Normal animals injected by saline. Control animals injected by anisodine. Anisodine caused mistake of memory. The results are listed as the following table.

TABLE 3

Effect of HUE and CLE on memory (1)

| Group | Increasing memory (%) |
|---|---|
| Normal | 100 |
| HUE (0.1 mg/kg) | 150 |

TABLE 3-continued

Effect of HUE and CLE on memory (1)

| Group | Increasing memory (%) |
|---|---|
| HUE (0.5 mg/kg) | 210 |
| HUE (1.0 mg/kg) | 350 |

TABLE 4

Effect of HUE and CLE on memory (2)

| Group | Number of animal | Dose (mg/kg) | Number of mistake |
|---|---|---|---|
| Normal | 10 | 0 | 5.0 ± 1.2 |
| Control | 10 | 0 | 38.5 ± 4.0 |
| HUE | 10 | 50 | *10.8 ± 1.5 |
| CLE | 10 | 50 | *11.2 ± 2.0 |
| HUE + CLE | 10 | 50 + 50 | *7.8 ± 1.0 |

*P < 0.01, compared with control group

The data of Table 3 and 4 indicated that HUE and CLE significantly decreases mistake of memory and increases memory.

EXAMPLE 12
Effect of HUE and CLE on Protein Synthesis

It is known that an age-dependent decline in animal brain protein synthesis. The decreased incorporation of amino acids into proteins can be observed in vitro including brain slices, brain cell suspensions, cell free brain homogenate preparations from older animals. Four months of male mice of DBA/2 strains used in experiment. Mice of HUE group injected HUE and dose was 0.1, 0.5 and 1.0 mg/kg. Mice of control group were injected by same value of saline. Mice killed and brain was rapidly removed. Cell free brain homogenate preparations used in experiment. ($^{14}$C) leucine mixed with homogenate suspension was incubated at 37° C. Homogenate precipitated with 10% trichloroacetic acid (TCA) and filtered onto glass fiber filters. The filters were washed with phosphate-buffered saline and placed in scintillation vials 10 ml of scintillation solution (which containing 0.5% and 0.00% of POPOP) were added to digested solution and determined at LSC and radioactive emissions were counted.

The data are listed in the following table.

TABLE 5

Effect of HUE and CLE on protein synthesis

| Group | CPM | P |
|---|---|---|
| Control | 901 | <0.01 |
| HUE (1.0 mg/kg) | 2640 | <0.01 |
| CLE (1.0 mg/kg) | 1580 | <0.01 |
| HUE (1.0 mg/kg) + CLE (1.0 mg/kg) | 3441 | <0.01 |

The data of Table 5 indicated that HUE significantly increases protein synthesis of brain of older mice and CLE strengthens the action of HUE.

EXAMPLE 13
Effect of HUE on Postischemic Generation of Superoxide Anion of Pig Brain Reperfusion injury after prolonged ischemia appeared to oxygen species of cerebral. The superoxide dismutase (SOD)-inhibitable nitroblue tetrazolium (NBT) reduction was determined as an index of superoxide anion generation in pig brain. In present study, effect of HUE on postischemic SOD-inhibitable NBT reduction was determined.

Piglets (1 kg) of either sex were anesthetized Anesthesia was maintained with α-chloralose. A catheter was inserted into a femoral artery to record blood pressure and to sample for blood gases and pH. Another catheter was placed in a femoral vein for injection of drugs. The trachea was cannulated, and the piglets were ventilated with room air. Body temperature was maintained at 37–38° C. with a water-circulating heating pad. Total cerebral ischemia was performed.

SOD-inhibitable NBT reduction was determined as an index of superoxide anion production. In control group, the piglets treated with vehicle (CSF). In treatment group, the piglets pretreated with HUE (0.5 mg/kg). SOD-inhibitable NBT reduction was determined for 20 minutes. For analysis, the slices were minced and homogenized in 1 N NaOH and 0.1% sodium dodecyl sulfate, the mixture centrifuged at 20,000 g for 20 min, the resulting supernatant discarded, and the pellet resuspended in 3 ml pyridine. The formazan was dissolved in the pyridine during hearing at 80° C. for 1 hour. Particulate matter was removed by a second centrifugation at 10000 g for 10 min. The concentration of formazan in the resulting solution was determined spectrophotometrically at 515 nm.

The experimental data are shown as the following table.

TABLE 6

Effect of HUE on superoxide anion of pig brain

| Group | Pmol NBT/mm$^2$, 20 min |
|---|---|
| Normal (N) | 2.8 ± 0.3 |
| Ischemia-reperfusion (C) | 12.9 ± 2.0 |
| Ischemia-reperfusion + HUE | 4.2 ± 0.5 |

The data of Table 6 indicated that HUE had markedly decreasing superoxide action of brain.

EXAMPLE 14
Effect of CIE and HUE on Calcium
Method of animal is as same as example 7.
$Ca^{++}$ concentration of brain cell was determined. The results are summarized in the following table.

TABLE 7

Effects of CLE and HUE on $Ca^{++}$ concentration

| Group | $Ca^{++}$ (µmol/L) | P |
|---|---|---|
| Control (C) | 112 | — |
| CLE | 220 | <0.01 |
| HUE | 160 | <0.01 |
| CLE + HUE | 310 | <0.01 |

P is compared with C group

Table 7 indicated that CLE markedly increases $Ca^{++}$ concentration of brain cells and HUE strengthens the action of CLE.

EXAMPLE 15
Effect of CLE and HUE on LTP
The long-term potentiation (LTP) is model of information stored in brain. LTP is as an index determined by electrophysiological method and express as mv in CAI area of brain.

TABLE 8

Effect of CLE and HUE on LTP

| Group | LTP (mv in CAI) |
|---|---|
| Control | 8 |
| CLE | 13 |
| HUE | 10 |
| CLE + HUE | 15 |

The data of Table 8 indicated that CLE could significantly increase LTP of brain and HUE could strengthen the action of CLE. Therefore, CLE and HUE improve memory.

EXAMPLE 16
Effect of CLE and HUE on Neurotransmitters
The effect of CLE and HUE on concentration of dopamine (DA) was examined. The method of animal is as same as mentioned previously. The results are summarized as the following table.

TABLE 9

Effect of CLE and HUE on DA

| Group | DA (ng/g brain) |
|---|---|
| Control | 880 ± 97 |
| CLE (10 mg/kg) | 1560 ± 102 |
| HUE (10 mg/kg) | 1280 ± 120 |
| CLE (10 mg/kg) + HUE (10 mg/kg) | 1850 ± 190 |

Table 9 indicated that CLE significantly increases DA in brain and HUE strengthens the action of CLE.

EXAMPLE 17
Effect of HUE and CLE on Synthesis of Nucleic Acid of Brain Cells
It is known that decline RNA content in cortical and cerebral cortex of AD. RNA of brain cell was determined.
Four months of male mice of DBA/2 strains used in experiment. Mice of treatment group injected HUE or CLE (dose was 1.0 mg/kg). Mice of control group were injected by same value of saline. Mice killed and brain was rapidly removed. Cell free brain homogenate preparations used in experiment. 0.5 µC $^3$H-U (20 µCi/mM) was mixed with 1 ml homogenate suspension was incubated at 37° C. Homogenate precipitated with 10% trichloroacetic acid (TCA) and filtered onto glass fiber filters. The filters were washed with phosphate-buffered saline and placed in scintillation vials 10 ml of scintillation solution (which containing 0.5% and 0.00% of POPOP) were added to digested solution and determined at LSC and radioactive emissions were counted.

The data are listed in the following table.

TABLE 10

Effect of HUE and CLE on RNA synthesis

| Group | CPM |
|---|---|
| Control (saline) | 1280 |
| HUE | 1860 |
| CLE | 1540 |
| HUE + CLE | 2280 |

The data of Table 10 indicated that HUE and CLE just increases $^3$H-U into RNA lightly, but HUE+CLE could significantly increase RNA synthesis.

The preparation of drugs, which can be accomplished by the extraction methods set forth above or any conventional methods for extracting the active principles from the plants. The novelty of the present invention resides in the mixture of the active principles in the specified proportions to produce drugs, and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, capsules, tablets, syrups, elixirs, and solutions for parenteral injection with specified ranges of drugs concentration.

In addition, the present invention provides novel methods for treating and preventing a variety of cancer conditions and control cancer cells with produced safe pharmaceutical agent.

It will thus be shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed is:

1. A botanical drug composition for treatment of Alzheimer's disease (AD) comprises 10~90% by weight of the drug of Huperzine (HUE) and 10~90% by weight of the drug of Clausenamide (CLE).

2. The botanical drug composition of claim 1 wherein the amount is 50% by weight of the drug of HUE and 50% by weight of the drug of CLE.

3. A botanical drug composition of claim 1 wherein the amount is orally sufficient to treat Alzheimer's disease composition is about 25–300 mg or intramuscularly 5–100 mg daily of 50% by weight of the drug of HUE and 50% by weight of the drug of CLE.

4. A botanical drug composition of claim 1 wherein the amount is orally sufficient to treat Alzheimer's disease and increase memory is about 25–300 mg and intramuscularly 5–100 mg daily of 50% by weight of the drug of HUE and 50% by weight of the drug of CLE.

5. A botanical drug composition of claim 1 wherein the amount is orally sufficient to treat Alzheimer's disease and decrease effect of amyloid protein is about 25–300 mg or intramuscularly 5–100 mg daily of 50% by weight of the drug of HUE and 50% by weight of the drug of CLE.

6. A botanical drug composition of claim 1 wherein the amount is orally sufficient to treat Alzheimer's disease and increase protein synthesis of old brain is about 25–300 mg or intramuscularly 5–100 mg daily of 50% by weight of the drug of HUE and 50% by weight of the drug of CLE.

7. A botanical drug composition of claim 1 wherein the amount is orally sufficient to treat Alzheimer's disease and increase RNA synthesis of old brain is about 25–300 mg or intramuscularly 5–100 mg daily of 50% by weight of the drug of HUE and 50% by weight of the drug of CLE.

8. A botanical drug composition of claim 1 wherein the amount is orally sufficient to increase calcium in brain is about 25–300 mg or intramuscularly 5–100 mg daily of 50% by weight of the drug of HUE and 50% by weight of the drug of CLE.

9. A botanical drug composition of claim 1 wherein the amount is orally sufficient to treat Alzheimer's disease and decrease superoxide anion is about 25–300 mg or intramuscularly 5–100 mg daily of 50% by weight of the drug of HUE and 50% by weight of the drug of CLE.

10. A botanical drug composition of claim 1 wherein the amount is orally sufficient to treat Alzheimer's disease and increase long-term potentiation is about 25–300 mg or intramuscularly 5–100 mg daily of 50% by weight of the drug of CLE and 50% by weight of the drug of HUE.

11. A botanical drug composition of claim 1 wherein the amount is orally sufficient to treat Alzheimer's disease and increase dopanmine is about 25–300 mg or intramuscularly 5–100 mg daily of 50% by weight of the drug CLE and 50% by weight of the drug HUE.

* * * * *